United States Patent [19]

Di Napoli

[11] Patent Number: 5,986,129
[45] Date of Patent: Nov. 16, 1999

[54] PROCESS FOR PRODUCING RHEIN AND DIACERHEIN

[75] Inventor: Guido Di Napoli, Collonge-Bellerive, Switzerland

[73] Assignee: Laboratoire Medidom S.A., Geneve, Switzerland

[21] Appl. No.: 08/903,663

[22] Filed: Jul. 31, 1997

[30] Foreign Application Priority Data

Jul. 31, 1996 [IT] Italy .................................. MI96A1656

[51] Int. Cl.$^6$ .......................... C07C 59/76; C07C 67/02
[52] U.S. Cl. ........................................... 562/461; 560/254
[58] Field of Search ............... 562/461; 560/254

[56] References Cited

U.S. PATENT DOCUMENTS

| 3,089,879 | 5/1963 | Serres, Jr. et al. . | |
|---|---|---|---|
| 4,346,103 | 8/1982 | Friedmann . | |
| 5,066,820 | 11/1991 | Helwig et al. | 552/249 |
| 5,652,265 | 7/1997 | Vittori et al. | 514/548 |

FOREIGN PATENT DOCUMENTS

| 0410315 | 1/1991 | European Pat. Off. . |
| 0636602 | 2/1995 | European Pat. Off. . |
| 80407 | 10/1894 | Germany . |
| 4945050 | 9/1972 | Japan . |
| 1578452 | 11/1980 | United Kingdom . |

*Primary Examiner*—Deborah C. Lambkin
*Attorney, Agent, or Firm*—Hedman, Gibson & Costigan

[57] ABSTRACT

The following description sets forth a process for producing rhein, diacerhein and other diacyl derivatives thereof, which comprises the following steps: treatment of a diphenylketone

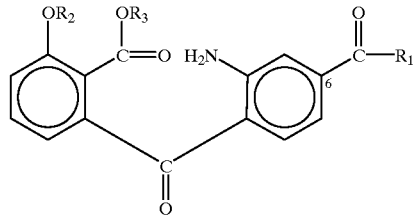

in which $R_1$ is —OR', —NR'R", —SR', where R' and R" are H, an alkyl or aromatic group; $R_2$ is H or a protective group, $R_3$ is —OH or $C_1$–$C_4$ alkyl, with an acid or superacid to give a 1-aminoanthraquinone derivative, diazotisation, replacement of the —$NH_2$ group by —OH, optional removal of the protective group, and acylation.

20 Claims, No Drawings

PROCESS FOR PRODUCING RHEIN AND DIACERHEIN

FIELD OF THE INVENTION

The present invention relates to a process for producing diacerhein from synthetic raw materials.

PRIOR ART

Rhein and several analogues thereof, the 1,8-diacyl derivative (diacerhein) being particularly important, are known for use in the treatment of degenerative diseases of the joints, such as osteoarthritis and connective tissue matrix diseases, for example osteoporosis and rheumatoid arthritis (GB 1,578,452).

Diacerhein is commercially available in the form of pharmaceutical preparations, such as Artrodar $^R$.

The only process for diacerhein synthesis utilized at present on a commercial scale is based on the use of aloin as starting material (European patent application No. 0 636 602 A1, by the Applicant). DE 80,407 and U.S. Pat. No. 3,089,879-A describe ring closure of 2,4'-benzophenone dicarboxylic acid to 2-carboxy-antraquinone by treatment with sulphuric acid.

Japanese application JP 49/45050 reports acid catalyzed cyclization of 2-(2'-aminobenzoyl)-benzoic acid to 1-aminoantraquinone.

In principle, two isomeric substituted 1-aminoantraquinones can be formed by cyclization of substituted 2-(2'aminobenzoyl)-benzoic acid. So these documents do in no way suggest that ring closure to 1-aminoantraquinone of diarylketones of formula (II) according to step a) of the present process as below illustrated allows the isomeric derivative of formula (III) to be obtained in high yield and in pure form.

TECHNICAL PROBLEM

Aloin is obtained from natural sources via laborious extraction and purification procedures consuming large amounts of vegetable raw materials.

Furthermore, since the market price of the raw material of vegetable origin fluctuates periodically, it is hardly possible to develop large-scale commercial processes manufacturing products from said raw material at the estimated cost. This is a serious disadvantage in the pharmaceutical sector, the prices of pharmaceuticals being strictly governed by the regulations in force.

Therefore, the need for a commercial-scale process for the production of diacerhein of good purity and in satisfactory yields not requiring the use of aloin or other raw materials of extractive origin is deeply felt.

SUMMARY

The Applicant has surprisingly found a process for producing rhein and related diacyl derivatives, e.g. diacerhein, of formula (I)

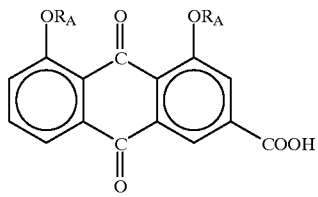

(I)

in which $R_A$ is H, acyl, alkyl or aromatic group, comprising the steps of:
a) treating a diphenylketone of formula (II)

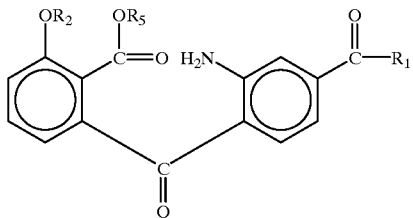

(II)

in which $R_1$ is —OH, —OR', —NH$_2$, —NHR', —NR'R", —SH or —SR', where R' and R", which may be the same or different one from another, each represents alkyl or aromatic groups,
$R_2$ is H or a protective group of the —OH function,
$R_5$ is H or $C_1$–$C_4$ alkyl,
with a strong concentrated acid (e.g. superacid) to give the 1-aminoanthraquinone derivative of formula (III)

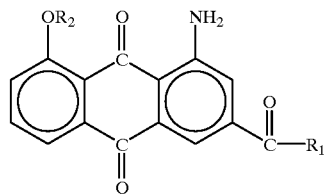

(III)

in which $R_1$ and $R_2$ are as defined above;
b) converting the —NH$_2$ group to —OH, via the following steps:
b') treating the derivative of formula (III) obtained in step a) with a diazotising agent, and
b") warm treating the product resulting from step b') with a strong acid in an aqueous medium to give the compound of formula (IV)

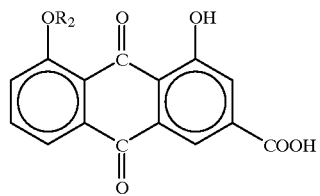

(IV)

in which $R_2$ is as defined above;
c) when $R_2$ is a protective group, removing $R_2$ in any process step, on the compound of formula (II), (III) or (IV), in which $R_2$ is a protective group as defined above, to give the rhein of formula (V)

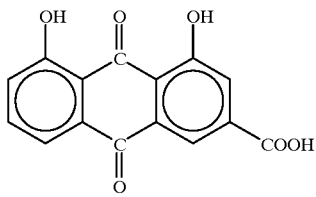
(V)

d) when $R_A$ is acyl, treating the rhein of formula (V) with an acylating agent.

The rhein of formula (V) may be optionally converted to the corresponding ethers of formula (I), in which $R_A$ is an alkyl or aromatic group, by conventional methods, e.g. by treatment with bases (e.g. NaH) and with the corresponding etherifying agents, e.g. alkylating agents, such as $R_A$Hal halides., where $R_A$ is the alkyl or aromatic group and Hal is a halogen.

This invention also provides a diphenylketone of formula (II), the 1-aminoanthraquinone derivative of formula (III), a compound of formula (IV) and the diazo derivative of formula (VI) described hereinafter.

It is a further object of the present invention to provide a process for producing a diphenylketone of formula (II) as defined in the aforementioned step a), comprising the steps of:

1) treating the phthalic acid derivative of formula (VII)

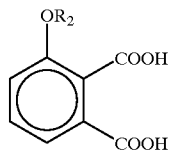
(VII)

in which $R_2$ is a protective group of the —OH function, with a hydroxylated compound, $R_3$OH, in which $R_3$ is an alkyl group, in the presence of a Cu(I) salt, in an acid medium, to give a monoester of formula (VIII)

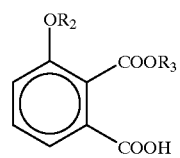
(VIII)

in which $R_2$ and $R_3$ are as defined above for this step;

2) treating the derivative of formula (VIII) obtained in step 1) with a halogenating agent of the carboxylic function to give an acyl halide of formula (IX)

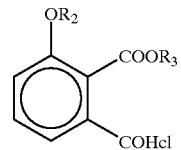
(IX)

in which $R_2$ and $R_3$ are as defined under 1), and Hal is a halogen;

3) treating the resulting derivative of formula (IX) with the derivative of formula (X)

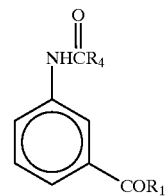
(X)

in which $R_1$ is —OR', —NHR', —NR'R" or —SR', and where R', R", $R_4$, which may be the same or different one from another, each represents alkyl (identical to or different from $R_3$) or aromatic groups, in the presence of a Friedel-Crafts catalyst, to give the protected diphenylketone of formula (XI)

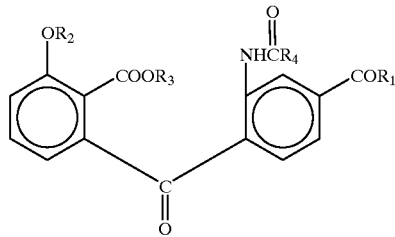
(XI)

in which $R_1$, $R_3$ and $R_4$ are as defined under 2) and $R_2$ is as defined under 1);

4) treating the protected diphenylketone of formula (XI) with a strong base, in an aqueous medium, and acidifying to give the diphenylketone of formula (II)A

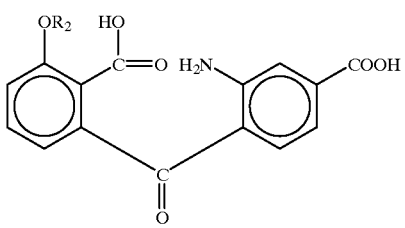
(II)A in which $R_2$ is as defined under 1).

The derivative of formula (II)A may be converted to the corresponding derivatives of formula (II), in which $R_1$ is —OR', —NR'R", —NHR', —SH or —SR' as defined above, e.g. by treatment with the corresponding alcohol, amine or thiol (e.g. with R'OH, R'R"NH or R'SH), by conventional methods.

The invention also provides dimethylketones of formulas (XI) and (II)A.

The process of the invention produces pure diacerhein in high yields. While the products obtained by the processes of the prior art always contain aloe-emodin at least in trace amounts as a result of the use of raw materials of natural origin (e.g., extracts of senna leaves or barbaloin)—said impurity exerting mutagenic action even in amounts as low as 70 ppm—the intermediates and final products obtained by the claimed process are totally free from aloe-emodin, i.e. no ppm or even ppm fractions thereof are present, since the present process exclusively utilizes aloe-emodin free synthetic starting materials, which, in no process phase, bring about formation of said impurity. Also, this invention further extends to i) compounds selected among the derivatives of formula (I), in which $R_A$ is H, acyl, alkyl or aromatic group, in particular diacerhein and pharmaceutically and cosmetically acceptable salts or derivatives thereof (e.g. esters, amides or thioesters), ii) pharmaceutical compositions for human or veterinary use containing a therapeutically effective amount of at least one of said compounds, combined with at least one pharmaceutically acceptable excipient and/or diluent, and optionally with one or more auxiliary substances, and iii) cosmetic preparations comprising at least one of said compounds, characterized in that said compounds, compositions and cosmetic preparations are completely free from aloe-emodin and/or from the derivatives of formula (I) analogous thereto, in which the —$CH_2OH$ group replaces the —COOH group.

The pharmaceutical compositions and cosmetic preparations of the present invention may be prepared by conventional methods.

The present pharmaceutical compositions free form aloe-emodin find the same therapeutic application (especially in human therapy), known for compounds of formula (I), in particular in the treatment of inflammatory states such as degenerative joints diseases, and are administered at unit dosages and daily dosages known for present derivatives of formula (I).

DETAILED DESCRIPTION OF THE INVENTION

As used herein, the alkyl groups are preferably $C_1$–$C_{20}$ alkyl groups and more preferably short-chain alkyl groups (e.g. $C_1$–$C_4$). Furthermore, saturated, straight or branched alkyl groups are preferred; however, they may optionally contain one or more unsaturations, e.g. one or more double bonds and/or be substituted, e.g., with alkoxy or phenoxy groups.

The aromatic substituents optionally present in the $R_1$ group or as $R_3$, $R_4$ or $R_B$ groups are preferably carbocyclic (monocyclic or polycyclic) $C_6$–$C_{20}$ aromatic groups, e.g. phenyl.

When $R_A$ is acyl, it may in particular be $R_BCO$-, where $R_B$ is an alkyl or aromatic group, typically $C_1$–$C_4$ alkyl.

The R', R", $R_3$ and $R_4$ groups are preferably short-chain alkyl groups, typically $C_1$–$C_4$ alkyl groups, i.e. containing 1 to 4 carbon atoms, more preferably —$CH_3$ groups.

In the derivatives of formula (II), $R_5$ is preferably H and, when $R_5$ is $C_1$–$C_4$ alkyl, is preferably —$CH_3$.

$R_2$ is typically a protective group removable in an acid medium and stable to the bases, preferably an alkyl group, typically saturated and having a straight or branched short chain (e.g. $C_1$–$C_4$), preferably —$CH_3$.

The $R_1$, $R_2$, $R_3$ and $R_4$ groups, present in the various chemical intermediates mentioned herein, may be varied, from one step to the other of the claimed processes, by known methods, depending on the requirements and according to the meanings reported herein or to equivalent meanings.

For the purposes of the present invention, preferred groups of compounds are of formulas (II) and (III) above, in which $R_1$ is —OH, $R_2$ is a saturated straight or branched alkyl group containing 1 to 4 carbon atoms ($C_1$–$C_4$), and for compounds of formula (II), $R_5$ is H; especially preferred are compounds of formulas (II) and (III) above in which $R_1$ is —OH, $R_2$ is —$CH_3$, and for compounds of formula (II), $R_5$ is H.

The compounds of formula (III) in which $R_1$ is —OH, may be converted to the corresponding compounds of formula (III), in which $R_1$ is OR', by treatment with an alcohol R'OH, in the presence of an acid catalyst, according to conventional methods.

Out of the compounds of formula (IV), the compounds in which $R_2$ is a saturated, straight or branched $C_1$–$C_4$ alkyl group, and in particular $CH_3$, are preferred.

When $R_1$ is —OR', —NR'R" or SR', $R_1$ conversion to —OH typically takes place in an aqueous acid medium, in steps b') or b"), and especially in step b"). yielding the corresponding phenol derivative of formula (IV) wherein the carboxyl function is free; alternatively, it may be carried out by a further hydrolysis step, i.e. acid or basic.

Preferably, the reaction mixture coming from diazotisation (step b') is directly subjected to step b") without prior isolation of the intermediate diazo derivative.

Step c), i.e. removal of protective group $R_2$, is preferably a step of acid hydrolysis, in an aqueous medium, of the compound of formula (II) or (III) or (IV), more preferably of formula (IV), in which $R_2$ is a protective group removable in an acid medium, typically $C_1$–$C_4$ alkyl.

Step c) is preferably carried out as the last step of the synthesis after performing, in sequence, steps a), b') and b"), on the compound of formula (IV) coming from step b"), in which $R_1$ is as defined above and $R_2$ is a protective group as defined above.

According to a preferred embodiment of the present invention, step a) utilizes the diphenylketone of formula (II), in which $R_5$ is H, $R_1$ is —OH, and $R_2$ is a $C_1$–$C_4$ alkyl group, preferably saturated, straight or branched, more preferably $CH_3$, to give the corresponding 1-aminoanthraquinone derivative of formula (III), in which $R_1$ is —OH and $R_2$ is a saturated, straight or branched $C_1$–$C_4$ alkyl group, preferably $CH_3$;

the reaction mixture from step b') is directly subjected to step b"), without prior isolation of the intermediate diazo derivative, to give the corresponding phenol derivative of formula (IV), in which $R_2$ is a saturated, straight or branched $C_1$–$C_4$ alkyl;

in step c), the derivative of formula (IV) as obtained above is subjected to acid hydrolysis to give the rhein of formula (V).

According to a still more preferred embodiment of the present invention, the derivative of formula (I) is diacerhein, in which $R_A$ is —$OCOCH_3$. Therefore, the process according to the present invention comprises acetylation (step d).

The strong acids suitable for the conversion of diphenylketone of formula (II) to the 1-aminoantraquinone derivative of formula (III) according to the present invention are for instance either mineral (inorganic) or organic acids, such as sulphuric acid and $CF_3SO_3H$. For the present purposes, concentrated acids typically have a concentration of about at least 90%, e.g. of about 95%–98% weight by weight (w/w) of acid, e.g. in water.

In present step a), superacids such as fuming sulphuric acid ($H_2SO_4.SO_3$, also known as oleum, with variable amount of $SO_3$ or $CF_3SO_3$ can be used, or concentrated sulphuric acid (e.g. about 95%–98% w/w). According to particular embodiments of the present invention, concentrated sulphuric acid or $CF_3SO_3H$ can be used, more preferably $CF_3SO_3H$.

Step a) is preferably carried out at a temperature approximately ranging from 0° C. to 250° C., preferably from 100° C. to 200° C., and more preferably from about 140° C. to 160° C.

For example, the diphenylketone of formula (II) and the selected strong concentrated acid are mixed under stirring at a temperature ranging from 0° C. to room temperature (about 20° C. to 30° C.); then the temperature is gradually raised preferably to a value ranging from about 100° to about 200° C., typically at least about 140° C. to 160° C.

The diphenylketone of formula (II)/acid ratio typically ranges from 0.5:1 to 4.75:1, e.g. about 1:3, expressed as mmols of product (II) per ml of strong acid.

The product of formula (III) is isolated by conventional methods: in particular it precipitates from the reaction medium, generally in the form of crystals, after neutralization with a strong base, e.g. NaOH, preferably added at a low temperature. e.g. 4° C. to 8° C., and is separated from the liquid phase by conventional methods, e.g. filtration.

Diazotisation (step b') is preferably carried out by cold treating the product of formula (II) with nitrous acid, in an aqueous medium; the reaction temperature preferably ranges from 0° C. to 8° C., more preferably from about 0° C. to 5° C.

Nitrous acid is preferably generated in the reaction medium by the action of a strong acid (e.g. an inorganic acid, such as $H_2SO_4$, or an organic acid, such as $CF_3SO_3H$, preferably $H_2SO_4$) on a nitrite, typically an alkali metal nitrite, such as $NaNO_2$.

For example, step b') is carried out with $NANO_2$, in a concentrated $H_2SO_4$/water mixture in a ratio ranging from 1:1 to 1:3 (volume/volume =v/v).

The diazotising agent is typically used in molar excess of the compound of formula (III), in a quantity ranging, e.g., from about 1.1 to 2.0 mol, preferably of about 1.5 mol per mol of (III).

The diazotised intermediate of formula (VI)

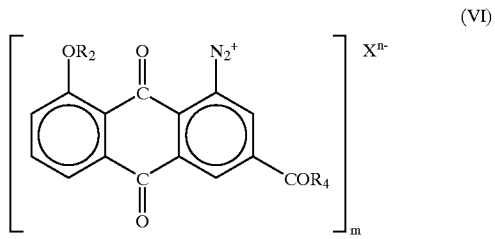

in which $R_1$ and $R_2$ are defined as for the dimethylketone of formula (II), can be isolated from the medium of diazotisation (step b'), e.g. by filtration.

X is the anion of the strong acid, in whose presence diazotisation is carried out;

n is the number (integer) corresponding to the number of negative charges of said anion;

when $R_1$ is H, m is (n-1), or, when $R_1$ is different from H, m=n. The diazo derivative of formula (VI) is preferably the one in which $R_1$ is —OH, and $R_2$ is $C_1$–$C_4$ alkyl, in particular $CH_3$; furthermore, X is preferably $SO_4^{2-}$(n=2), and m is 1.

In step b") the strong acid is, e.g., an inorganic acid, such as sulphuric acid, or an organic acid, such as $CF_3SO_3H$; sulphuric acid is typically used.

Step b") is generally carried out at a temperature ranging from 100° C. to 250° C., preferably of about 140° C. to 150° C. Under typical conditions, the reaction medium of steps b') and b") is a strong acid/water mixture in a ratio preferably ranging from 1:0.5 to 1:5, more preferably from 1:1 to 1:3 (v/v).

Furthermore, step b') is preferably carried out with ratios of the derivative of formula (III) to the reaction medium ranging from 1:0.5 to 1:5, typically 1:3, expressed as mmols of (III) per ml of reaction medium; step b") is preferably carried out with ratios of substrate [derivative of formula (III) or derivative of formula (VI)] to the reaction medium typically equal to about 1:3, expressed as mmols of the derivative of formula (III) or (VI) per ml of reaction medium (typically a strong acid/water mixture).

The resulting phenol derivative of formula (IV) is easily isolated from the acid reaction mixture by cooling to room temperature and collecting the precipitate, e.g. by filtration.

As mentioned above, step b") is preferably carried out on the reaction mixture from step b'), optionally diluted, without prior isolation of the diazotisation product. For example, diazotisation is carried out in an acid aqueous medium, e.g. by optionally diluting with additional strong acid/water mixture the reaction mixture from step b'), then heating to the temperature of step b").

Acid hydrolysis as per step c) is preferably carried out at a temperature ranging from about 90° C. to about 160° C., more preferably from about 100° C. to about 120° C.

Preferably, step c) is carried out with concentrated HBr (about 48% HBr aqueous solution) and glacial acetic acid as diluent; the temperature is preferably the reflux temperature of the reaction mixture.

The quantity of concentrated HBr ranges, e.g., from about 0.1 ml to 10 ml, typically from 0.5 ml to 3 ml of concentrated HBr per mmol of substrate of formula (II), (III) or (IV).

The quantity of glacial acetic acid ranges about from 5 to 20 ml, e.g. about 10 ml per mmol of substrate to be treated.

Under the conditions reported above, the reaction product from step c), in particular the rhein of formula (V), generally precipitates in the reaction medium at room temperature, wherefrom is separated by conventional methods, e.g. by filtration in vacuo; then it is preferably purified by crystallization, e.g. from an alcohol, such as methanol.

The synthesis reactions as per steps a), b'), b") and c) described above are completed within short times, generally ranging from about 15 min. to 2-14 3 hrs., and give highly pure products in high yields. Preferably, the derivative of formula (I) is the one in which $R_A$ is —$COCH_3$ (diacerhein).

Preferably, the rhein of formula (V) is prepared through steps a), b'), b") and c) defined above and converted to the acyl derivative, preferably diacerhein, via step d).

Treatment with the acylating agent as per step d) is carried out at temperatures preferably ranging from about 50° C. to about 100° C., e.g. from about 70° C. to 90° C.

The acylating agent is, e.g., the anhydride or acyl halide of the $R_B$COOH acid, where $R_B$ is as defined above.

The halide is typically used in the presence of a base as protons acceptor, and the anhydrides are used in the presence of an acid or basic catalyst; the acid catalyst may be, e.g., an organic acid, such as acetic acid, methanesulphonic acid, trifluoromethanesulphonic acid, or an inorganic acid, such as concentrated sulphuric acid, preferably $H_2SO_4$; the basic catalyst may be, e.g., an organic base, typically an alkali metal acetate, such as sodium acetate, or an inorganic base, such as an alkali metal bicarbonate, e.g. $NaHCO_3$.

Preferably, the acylating agent is acetic anhydride, an acetyl halide, such as the chloride, typically used in the presence of a base as a protons acceptor, or hexachloroacetone.

Acetic anhydride in the presence of an acid or basic catalyst is preferably used.

The acylating agent (typically acetic anhydride) is generally in stoichiometric excess in respect of rhein, e.g. it amounts to from 2.0 to 5.0 mols, preferably 3.0 mols per mol of rhein.

Preferably, rhein is treated with acetic anhydride, in glacial acetic acid as reaction solvent, the solvent being in an amount ranging, e.g. from about 0.5 to about 5 ml, typically of about 1 ml per mmol of rhein, in the presence of a catalytic quantity of concentrated $H_2SO_4$. Diacerhein is easily isolated from the reaction medium as it precipitates by cooling to room temperature and is separated by conventional methods, such as filtration.

The diphenylketone of formula (II) is a novel product synthesized by the Applicant from commercially available compounds. The derivative or-formula (VII) is obtained, e.g., by oxidation of the dimethylbenzene derivative of formula (XII)

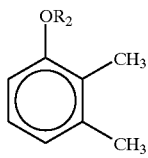

(XII)

in which $R_2$ is a protective group of the —OH function, preferably a saturated, straight or branched $C_1-C_4$ alkyl group, with an oxidizing agent, preferably a hypochlorite (such as NaClO), and with an alkyl halide, preferably containing 1 to 6 carbon atoms (such as n-butylbromide), in the presence of a transition metal salt (preferably a Ru(III) salt, such as $RuCl_3$). preferably operating in an aqueous medium, at alkaline pH, at a temperature preferably ranging from 30° C. to 100° C., preferably of about 40° C. to 60° C.

The oxidation of the compound of formula (XII) is generally carried out in water, preferably at about pH 8-9, this value being maintained by addition of a strong base, such as NaOH.

Preferably, the oxidant used in respect of the dimethylbenzene derivative of formula (XII) amounts to from 2 to 5 mols, e.g. 3 mols; the halide is preferably in a stoichiometric amount in respect of the derivative of formula (XII); the catalyst is typically in an amount ranging from 1% to 30% in mols, preferably from 10% to 25% in mols in respect of the derivative of formula (XII).

Several derivatives of formula (XII) are commercially available or may be prepared by conventional methods.

Preferred derivatives of formula (VII) above are the ones in which $R_2$ is a saturated, straight or branched $C_1-C_4$ alkyl group, especially $CH_3$.

Out of the derivatives of formula (VIII), particularly preferred are the ones in which $R_2$ and $R_3$, which may be the same or different one from the other, are $C_1-C_4$ alkyl groups, preferably saturated, more particularly the ones in which $R_2=R_3=CH_3$.

In step 1), the temperature preferably ranges from about 30° C. to 100° C., typically from about 50° C. to 70° C.

Furthermore, $R_3OH$ is preferably $CH_3OH$ and is preferably used as a reaction solvent, in an amount, e.g., ranging from 0.5 to 2 ml, preferably of 1 ml per mmol of the derivative of formula (VII).

Preferably, the Cu(I) salt is a halide, such as CuCl, and the acid is an inorganic strong acid, typically a hydrogen halide, such as HCl; furthermore, the Cu(I) salt and the acid are preferably used in a stoichiometric amount in respect of the compound of formula (VII), as well as up to 2 mols per mol of (VII).

Preferred derivatives of formula (IX) are the ones in which $R_2$ and $R_3$, which may be the same or different one from the other, are $C_1-C_4$ alkyl groups, preferably saturated, and especially the ones in which $R_2=R_3=CH_3$; furthermore, Hal is preferably Cl or Br and more preferably Cl.

The temperature of step 2) preferably ranges from about 50° C. to 120° C., more preferably from about 60° C. to 90° C.; the halogenating agent is, e.g., thionyl chloride, $PCl_5$ or $PCl_3$.

Typically, thionyl chloride is used, e.g., as a reaction medium, in a quantity typically ranging from about 1 to 2 ml per 100 mmols of the derivative of formula (VIII). The reaction is preferably carried out at the reflux temperature of the reaction mixture (about 78° C. to 80° C.).

Step 2) may be also carried out in the presence of a diluent or of an inert organic solvent.

Preferred derivatives of formula (X) are the ones in which $R_1$ is —OR', and R' and R4, which may be the same or different one from the other, are preferably a saturated, straight or branched $C_1-C_4$ alkyl, and more preferably the ones in which $R_1$ is —$OCH_3$ and $R_4$ is $CH_3$.

The temperature of step 3) preferably ranges from about 40° C. to 100° C., more preferably from about 40° C. to 60° C.

Furthermore, the catalyst is selected out of the catalysts commonly used in Friedel-Crafts reactions (alkylations or acylations) and is typically an aluminium halide, such as $AlCl$ Step 3) preferably utilizes stoichiometric ratios of the derivative of formula (X) to the derivative of formula (IX) and amounts of Friedel-Crafts catalyst typically ranging from 0.1% to 10% in mols, more typically from about 1% to 2% in mols in respect of the derivative of formula (IX).

According to a preferred embodiment of the present invention, step 3) is carried out in the absence of solvents, simply by mixing the substrates of formulas (IX) and (X) with the catalyst and raising the reaction temperature to the selected value. Alternatively, however, step 3) may be also carried out in the presence of diluents or of inert organic solvents.

Preferred derivatives of formula (XI) are the ones in which $R_1$ is —OR', and R, $R_2$, $R_3$ and $R_4$, which may be the same or different one from another, are preferably a saturated, straight or branched $C_1-C_4$ alkyl, more preferably the ones in which $R_1$ is —$OCH_3$ and $R_2=R_3=CH_3$.

In the hydrolysis (step 4), the temperature preferably ranges from 30° C. to 100° C. and more preferably is of about 80° C. Furthermore, the base is preferably an alkaline hydroxide, such as NaOH, said base being used in a quantity preferably ranging from about 0.5 to 1 mol per mol of compound of formula (XI).

Step 4) is preferably carried out in a water-alcohol mixture, alcohol being, e.g., methanol, ethanol, e.g. in 50:50 water/ethanol.

At the end of the reaction, diphenylketone (II)A is recovered from the reaction medium by acidification, typically with HCl.

Preferred derivatives of formula (II)A are the ones in which $R_2$ is a $C_1-C_4$ alkyl group, preferably saturated, and more typically $R_2=CH_3$.

The derivatives of formula (X), in which $R_1$ is —NR'R", —SR' or —OH can be obtained from the corresponding derivatives, in which $R_1$ is —OR' as above defined, by conventional methods.

The derivatives of formula (X), in which $R_1$ is —OR' as above defined, are e.g. prepared by esterification of 3-aminobenzoic acid, followed by acylation of the aminic function.

For example, 3-aminobenzoic acid is treated with an R'OH alcohol, where R' is as defined above and is preferably a $C_1-C_4$ alkyl group (more preferably $CH_3$), in the presence of an acid catalyst, preferably at a temperature ranging from 30° C. to 100° C., e.g. from 50° C. to 70° C. to give the corresponding ester of formula (XIII)

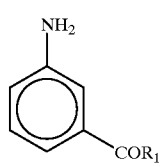

(XIII)

in which R' is as defined above and more preferably is $CH_3$.

R' OH is preferably $CH_3OH$ and is typically used as a reaction solvent; furthermore, the acid catalyst is, e.g. concentrated $H_2SO_4$, in a quantity ranging from 1 to 5 ml, e.g. 3 ml, per 100 mmols of substrate.

The resulting derivative of formula (XIII) is treated with an acylating agent, preferably with the $R_4COOH$ acid anhydride. where $R_4$ is as defined above and is preferably a saturated $C_1-C_4$ alkyl group, preferably in the presence of an acid catalyst. such as the $R_4COOH$ acid, at a temperature preferably ranging from about 80° C. to about 120° C. more preferably at about 100° C. to 120° C.

Preferably, $R_4$ is $CH_3$, the anhydride is acetic anhydride and the acid is acetic acid, used, e.g. as reaction solvents, the acid. e.g., in an amount of about 2 to 10 ml. preferably 5 ml. per 100 mmols of substrate of formula (X), and the anhydride in an amount of about 1 to 2 ml, e.g., about 1.2 to 1.4 ml, per 100 mmols of substrate of formula (XIII).

The compounds of formula (X) may be anyhow prepared by other conventional methods.

The following examples are conveyed by way of indication, not of limitation, of the present invention.

EXAMPLE 1

Preparation of the Intermediate of Formula (III) in which $R_1$ is —OH and $R_2$ is —$CH_3$ The intermediate of formula (II) (0.01 mol), in which $R_5$ is H, $R_1$ is —OH and $R_2$ is —$CH_3$, was suspended in 30 ml concentrated strong acid, such as $H_2SO_4$ or $CF_3SO_3H$, more preferably $CF_3SO_3H$. The resulting mixture was heated to 150° C. for 2 hrs. under constant stirring. After said 2 hr-period, the solution was cooled to room temperature and neutralized with 10% aqueous NaOH.

The precipitate was filtered, washed with water and evaporated to dryness, to give a crystalline product corresponding to the intermediate of formula (III) (0.0089 mol), in which $R_1$ is —OH and $R_2$ is —$CH_3$. Total yield 88%. Melting point 226° C.

The product was analysed by TLC on silica gel and identified by IR spectrometry.

The analytical values were in agrement with the theoretical values.

EXAMPLE 2

Preparation of the Intermediate of Formula (IV) in which $R_2$ is —$CH_3$

The intermediate of formula (III) (0.01 mol), in which $R_1$ is OH and $R_2$ is —$CH_3$, obtained as per Example 1. was dissolved in a 1:3 sulphuric acid/water mixture (v/v), in a quantity of about 20 to 35 ml.

The resulting mixture was cooled to 0° C. to 5° C., allowed to stir until complete dissolution of the intermediate of formula (III), and added with $NaNO_2$ (0.015 mol) dissolved in 10 ml cool water (50° C.).

The reaction mixture was left under stirring for an additional 15 min. and added with 100 ml of a 1:1 water-sulphuric acid mixture (v/v). The solution was heated to 150° C. for 1 hr. under constant stirring. After cooling to room temperature, the resulting precipitate was collected by filtration in vacuo, washed with water and dried under reduced pressure at 50° C. A yellow-brown crystalline solid was obtained (m.p. 261° C.). corresponding to the intermediate of formula (IV) (0.0085 mol) in which $R_2$ is —$CH_3$.

EXAMPLE 3

Preparation of Rhein [compound of formula (V)]

The product obtained as per Example 2 [intermediate of formula (IV) in which $R_2$ is —$CH_3$] was suspended in 100 ml glacial acetic acid containing a 48% HBr solution in water (10 ml). The reaction mixture was heated to reflux for 3 hrs., cooled to room temperature and filtered.

The precipitate obtained was collected by filtration in vacuo, washed with water and dried under reduced pressure.

Recrystallization from methanol gave a yellow-greenish needle-shaped product (m.p. 244° C. to 246° C.). Yield 79% to 83%.

Elemental analysis, IR and Rf values are in accordance with the values found for rhein [compound of formula (V)].

EXAMPLE 4

Preparation of Diacerhein

Rhein (0.01 mol) obtained as per Example 3 was suspended in 100 ml glacial acetic acid. The resulting suspension was added with acetic anhydride (0.03 mol) and one drop of concentrated sulphuric acid. and heated to 80° C. under stirring for 1 hr. The solution was allowed to cool to room temperature. A yellow-greenish precipitate was collected by filtration in vacuo, washed with water and dried under reduced pressure. Total yield 98%. Melting point 247° C.

IR spectrum: $v_{max}$ 1733 $cm^{-1}$ (ester), 1701 $cm^{-1}$ (carboxyl), 1689 $cm^{-1}$ (carbonyl).

Elemental analysis: Calcd for $C_{19}H_{12}O_8$: C, 61,96; H. 3.29; Found: C, 62.07; H 3.39.

The above data prove that the product obtained is identical with an authentic diacerhein sample. DIPHENYLONE OF FORMULA (II)A IN WHICH $R_2$ IS —$CH_3$

EXAMPLE 5

Preparation of Methoxyphthalic Acid [derivative of formula (VII) in which $R_2$ is $CH_3$]

A mixture was made up as follows: 0.1 mol of 2,3-dimethylmethoxybenzene [derivative of formula (XII) in which $R_2$ is $CH_3$], added with 0.3 mol of NaClO, as an aqueous solution containing 15% active Cl; n-butylbromide (0.1 mol); $RuCl_3.3H_2O$ (0.02 mol).

The mixture was vigorously stirred at 50° C. and the pH of the solution was maintained at 8-9 through the addition of 2M NaOH.

When the pH of the solution remained constant, the reaction mixture was allowed to stir for an additional 1 hr., cooled to room temperature and acidified with a concentrated $HCl-H_2O$ mixture until complete precipitation of methoxyphthalic acid. The precipitate was collected by filtration and dried under reduced pressure. The methoxyphthalic acid yield was 98%.

EXAMPLE 6

Preparation of Methoxyphthalic Acid Monomethylester [derivative of formula (VIII) in which $R_2=R_3=CH_3$]

A solution of methoxyphthalic acid obtained as per Example 5 (0.1 mol) in 100 ml methanol was added with CuCl (0.1 mol) and HCl (0.1 mol). The solution was heated to reflux for 30 min. The clear solution obtained was evaporated to dryness under reduced pressure. The residue obtained was dissolved in a 1:3 water-methanol mixture and acidified. The product was separated by cooling, collected by filtration and air dried. The product yield was 63–66%.

EXAMPLE 7

Preparation of Methoxyphthalic Acid Monomethylester Chloride [derivative of formula (IX) in which $R_2=R_3=CH_3$ and Hal is Cl]

The methoxyphthalic acid monomethylester obtained as per Example 6 (0.1 mol) was suspended in thionyl chloride (1.5 ml). The resulting suspension was slowly heated to reflux until complete dissolution of the solid material.

After refluxing for an additional 30 min., excess thionyl chloride was removed under reduced pressure and the residue was recrystallized from toluene.

The title product yield was 84%.

EXAMPLE 8 a) Preparation of 3-Aminobenzoic Acid Monomethylester [derivative of formula (XIII) in which $R_1$ is —$OCH_3$]

3-Aminobenzoic acid (0.1 mol) was added with 50 ml methanol. The mixture was cooled in an ice bath and slowly added with 3 ml concentrated $H_2SO_4$. The components were mixed and refluxed for 1 hr.

The solution was cooled, settled in a separatory funnel containing 50 ml water. The vessel was fed with 35 ml t-butylmethylether. After mixing, the aqueous layer was removed and the ethereal phase was washed first with 25 ml water and then with 25 ml 1.5M $NaHCO_3$. The ethereal phase was evaporated under an aspirating tube.

b) Preparation of 3-Aminobenzoic Acid Monomethylester N-Acetyl Derivative [derivative of formula (X) in which $R_1$ is —$OCH_3$ and $R_4$ is $CH_3$]

The 3-aminobenzoic acid monomethylester obtained as per a) above (0.1 mol) was added with acetic acid (5 ml).

The resulting mixture was heated slightly above 100° C. and the solution was allowed to stir.

The temperature was allowed to decrease to 100° C. and acetic anhydride (1.3 ml) was added. The mixture was left under stirring until the temperature lowered to 75° C. and water (1 ml) was added. Water was removed in vacuo and the resulting oily syrup was resuspended in cyclohexane (5 ml). The temperature was raised to remove the trace water from the syrup as a cyclohexane-water azeotrope. The title product yield was 89% to 93%.

EXAMPLE 9

Preparation of Diphenylketone of Formula (XI) in which $R_1$ is —$OCH_3$ and $R_2=R_3=R_4=CH_3$ Methoxyphthalic acid monomethylester chloride (0.1 mol) and 3-aminobenzoic acid monomethylester N-acetyl derivative were caused to react in a 10×100 mm tube.

The reaction mixture was cooled in an ice bath and added with anhydrous $AlCl_3$ (200 mg). The tube was sealed with a septum connected with a Teflon tube immersed in a moist cotton plug trapping the HCl being developed during the reaction. The tube content was carefully mixed and cautiously heated in a hot water vessel. Gaseous HCl evolution was controlled by repeatedly heating and cooling the reaction mixture. The reaction was continued for about 15 min. at 50° C. until gas evolution ceased completely.

The mixture was cooled in an ice bath and added with ice in small pieces (1 g). Each piece of ice was allowed to react before adding the successive piece. The tube content was carefully mixed, cooled to room temperature, added with 0.5 ml water and 5 ml t-butylether, and mixed. The aqueous phase was removed. Once extraction had been repeated, concentrated HCl (0.2 ml) in 0.5 ml water was added. The organic layer was transferred into a small test tube and evaporated to dryness.

Diphenylketone yield was 79%.

EXAMPLE 10

Hydrolysis of Diphenylketone of Formula (XI), in which $R_1$ is —$OCH_3$, $R_2=R_3=R_4=CH_3$, to give the dimethylketone of formula (II)A, in which $R_2$ is $CH_3$ The diphenylketone obtained as per Example 9 (0.1 ml) was treated with a 50:50 water-ethanol mixture (3 ml) containing NaOH (about 1.89 to 3.6 g). The mixture was cautiously heated to reflux in a sand bath for 30 min. Once the reaction had been completed, the solution was acidified, the precipitate was collected by filtration, and air dried. The product yield was 90%.

I claim:

1. Process for producing rhein and rhein derivatives of formula (I)

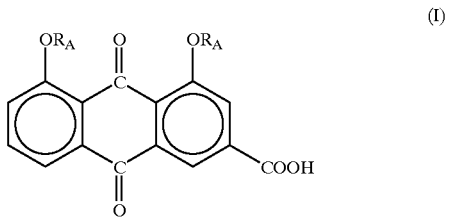

in which $R_A$ is H, acyl, alkyl or aromatic group comprising the steps of:

a) treating a diphenylketone of formula (II)

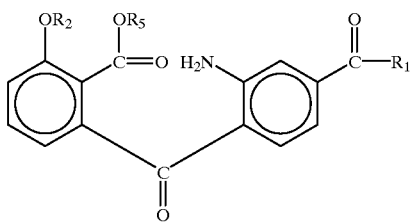

(II)

in which $R_1$ is —OH, —OR', —NH$_2$, —NHR', —NR'R", —SH or —SR', where R' and R", which may be the same or different one from another, each represents alkyl or aromatic groups, $R_2$ is H or a protective group of the —OH function, $R_5$ is H or $C_1$–$C_4$ alkyl, with a strong concentrated acid to give the 1-aminoanthraquinone derivative of formula (III)

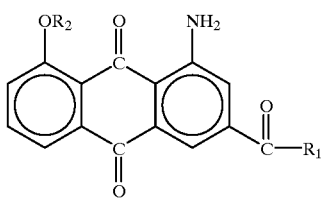

(III)

in which $R_1$ and $R_2$ are as defined above:

b) converting the —NH$_2$ group to —OH, via the following steps:

b') treating the derivative of formula (III) obtained in step a) with a diazotising agent, and b") warm treating the resulting product with a strong acid in an aqueous medium to give the compound of formula (IV)

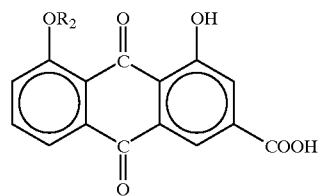

(IV)

in which $R_2$ is as defined above;

c) when $R_2$ is a protective group, removing $R_2$ in any process step, on the compound of formula (II), (III) or (IV), in which $R_2$ is a protective group as defined above, to give the rhein of formula (V)

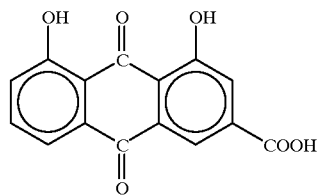

(V)

d) when $R_A$ is acyl, treating the rhein of formula (V) with an acylating agent, or, when $R_A$ is alkyl or aromatic group, with a base and with the corresponding etherifying agent.

2. A process as claimed in claim 1 for producing the derivative of formula (I) in which $R_A$ is —COCH$_3$ (diacerhein), wherein step d) is an acetylation step.

3. A process as claimed in claim 1, wherein:

the reaction mixture coming from diazotisation (step b') is directly subjected to step b") without prior isolation of the intermediate diazo derivative;

step c), i.e. removal of protective group $R_2$, is carried out as the last step of the synthesis on the compound of formula (IV) coming from step b"), in which $R_1$ is as defined above and $R_2$ is a protective group as defined above, after performing, in sequence, steps a), b') and b").

4. A process as claimed in claim 1, wherein:

step a) utilizes the diphenylketone of formula (II), in which $R_5$ is H, $R_1$ is —OH, and $R_2$ is a saturated, straight or branched $C_1$–$C_4$ alkyl group to give the corresponding 1-aminoanthraquinone derivative of formula (III), in which $R_1$ is —OH and $R_2$ is a saturated, straight or branched $C_1$–$C_4$ alkyl group;

the reaction mixture from step b') is directly subjected to step b"), without prior isolation of the intermediate diazo derivative, to give the corresponding phenol derivative of formula (IV), in which $R_2$ is a saturated, straight or branched $C_{1-4}$ alkyl;

in step c), the derivative of formula (IV) as obtained above is subjected to acid hydrolysis to give the rhein of formula (V).

5. A process as claimed in claim 1, wherein, in step a) the concentrated strong acid is concentrated H$_2$SO$_4$, fuming H$_2$SO$_4$ or CF$_3$SO$_3$H and the temperature ranges from 0° C. to 250° C.

6. A process as claimed in claim 1, wherein the temperature of step a) ranges from 100° C. to 250° C.

7. A process as claimed in claim 6, wherein the temperature of step a) ranges at least from 140° C. to 160° C.

8. A process as claimed in claim 1, wherein diazotisation (step b') is carried out by cold treatment of the product of formula (II) with nitrous acid in an aqueous medium.

9. A process as claimed in claim 8, wherein the temperature of step b') ranges from 0° C. to 8° C.

10. A process as claimed in claim 8, wherein, in step b'), the nitrous acid is generated in the reaction medium by the action of a strong acid on an alkali metal nitrite.

11. A process as claimed in claim 10, wherein the nitrite is NaNO$_2$ and the strong acid is H$_2$SO$_4$.

12. A process as claimed in claim 1, wherein the temperature of step b") ranges from 100° C. to 250° C.

13. A process as claimed in claim 12, wherein the temperature of step b") ranges from 140° C. to 150° C.

14. A process as claimed in claim 12, wherein the strong acid is $H_2SO_4$.

15. A process as claimed in claim 1, wherein steps b') and b") are carried out in a reaction medium consisting of a strong acid-water mixture in ratios ranging from 1:0.5 to 1:5 (v/v).

16. A process as claimed in claim 1, wherein step c) is an acid hydrolysis carried out at a temperature ranging from 90° C. to 160° C.

17. A process as claimed in claim 1, wherein step c) is carried out with concentrated HBr in glacial acetic acid as diluent.

18. A process as claimed in claim 2, wherein step d) is carried out at a temperature ranging from 50° C. to 100° C.

19. A process as claimed in claim 18, wherein the temperature ranges from 70° C. to 90° C.

20. A process as claimed in claim 18, wherein rhein is treated with acetic anhydride, in glacial acetic acid, in the presence of a catalytic quantity of concentrated $H_2SO_4$.

\* \* \* \* \*